US012144557B2

(12) United States Patent
Song et al.

(10) Patent No.: US 12,144,557 B2
(45) Date of Patent: Nov. 19, 2024

(54) ROBOTIC SURGICAL SYSTEM

(71) Applicant: National Yang Ming Chiao Tung University, Hsinchu (TW)

(72) Inventors: Kai-Tai Song, New Taipei (TW); Shih-Wei Chiu, New Taipei (TW); Bing-Yi Li, Taichung (TW)

(73) Assignee: National Yang Ming Chiao Tung University, Hsinchu (TW)

(*) Notice: Subject to any disclaimer, the term of this patent is extended or adjusted under 35 U.S.C. 154(b) by 145 days.

(21) Appl. No.: 18/050,332

(22) Filed: Oct. 27, 2022

(65) Prior Publication Data
US 2024/0041526 A1 Feb. 8, 2024

(30) Foreign Application Priority Data

Aug. 3, 2022 (TW) .................................. 111129194

(51) Int. Cl.
*A61B 34/10* (2016.01)
*A61B 34/00* (2016.01)
(Continued)

(52) U.S. Cl.
CPC .............. *A61B 34/10* (2016.02); *A61B 34/20* (2016.02); *A61B 34/25* (2016.02); *A61B 34/30* (2016.02);
(Continued)

(58) Field of Classification Search
None
See application file for complete search history.

(56) References Cited

U.S. PATENT DOCUMENTS 8,992,580 B2 3/2015 Bar et al.
2017/0273595 A1* 9/2017 Lee .......................... A61B 5/06
(Continued)

FOREIGN PATENT DOCUMENTS

TW I618036 B 3/2018
TW I697317 B 7/2020

OTHER PUBLICATIONS

Qian et al., "ARssist: augmented reality on a head-mounted display for the first assistant in robotic surgery," Healthcare Technology Letters, 2018, vol. 5, Iss. 5, pp. 194-200. (Year: 2018).*
(Continued)

*Primary Examiner* — Joel Lamprecht
*Assistant Examiner* — Ashish S Jasani
(74) *Attorney, Agent, or Firm* — MLO, a professional corp.

(57) ABSTRACT

A robotic surgical system includes a surgical robot holding a surgical instrument, a wearable device worn by a person, a camera for capturing images, and a computer device. The camera captures images of a base marker, and a dynamic reference frame disposed on an affected part of a patient. The computer device calculates a plurality of conversion relationships among different coordinate systems, and controls the surgical robot to move the surgical instrument according to a pre-planned surgical path and based on the conversion relationships. Furthermore, the computer device transmits data of a 3D model and the pre-planned surgical path to the wearable device, such that the wearable device is configured to present the 3D model in combination with the pre-planned surgical path as an AR image based on the conversion relationships.

6 Claims, 5 Drawing Sheets

(51) Int. Cl.
    A61B 34/20    (2016.01)
    A61B 34/30    (2016.01)
    A61B 90/00    (2016.01)
    A61B 90/50    (2016.01)

(52) U.S. Cl.
    CPC .............. *A61B 90/37* (2016.02); *A61B 90/50* (2016.02); *A61B 2034/102* (2016.02); *A61B 2034/105* (2016.02); *A61B 2034/107* (2016.02); *A61B 2034/2055* (2016.02); *A61B 2034/2057* (2016.02); *A61B 2090/365* (2016.02); *A61B 2090/3762* (2016.02); *A61B 2090/502* (2016.02)

(56) References Cited

U.S. PATENT DOCUMENTS

| | | | | |
|---|---|---|---|---|
| 2020/0093544 | A1* | 3/2020 | Azizian | G06F 3/04883 |
| 2021/0338337 | A1* | 11/2021 | Calloway | G06F 3/011 |
| 2022/0265357 | A1* | 8/2022 | Morvan | A61B 90/361 |
| 2022/0265364 | A1* | 8/2022 | Kim | A61B 34/25 |

OTHER PUBLICATIONS

Sun et al., "Fast and accurate online calibration of optical see-through head-mounted display for AR-based surgical navigation using Microsoft HoloLens," International Journal of Computer Assisted Radiology and Surgery, 15(11), pp. 1907-1919, Aug. 2020.

Lohou et al., "Preliminary Experiment of the Interactive Registration of a Trocar for Thoracoscopy with HoloLens Headset," Proc. International Conference on Image Analysis and Processing, 11752, pp. 694-703, Sep. 2019.

Jo and Song, "Supervised Control for Robot-Assisted Surgery Using Augmented Reality," Proc. of 2020 20th International Conference on Control, Automation and Systems (ICCAS 2020), pp. 329-334, Oct. 2020.

* cited by examiner

ROBOTIC SURGICAL SYSTEM

CROSS-REFERENCE TO RELATED APPLICATION

This application claims priority to Taiwanese Invention Patent Application No. 111129194, filed on Aug. 3, 2022.

FIELD

The disclosure relates to a robotic surgical system, more particularly to a robotic surgical system that involves automatic guiding of a robotic arm, and that includes augmented reality functionality.

BACKGROUND

In the field of robot assisted surgery, the application of image-guided surgery, in which a number of graphical images are used in different stages of a surgery (e.g., trajectory pre-planning, intraoperative guiding and monitoring, etc.), has become a popular topic. In the application of image-guided surgery, a human-machine visual interface may be provided to display preoperative images and intraoperative images on a screen, so as to provide the surgeon with surgery-related information. For example, in a surgery to implant a pedicle screw onto a pediculus arcus vertebrae of a patient (a surgery known as pedicle screw placement), a surgical drill may be first held by a robot arm to drill a pre-planned passage in the pediculus arcus vertebrae, and then the pedicle screw is implanted in the passage by the robot arm operating a surgical instrument. During the surgery and after the surgery, the intraoperative images obtained using computerized tomography (CT) scanning are displayed on the human-machine visual interface, such that the surgeon is enabled to determine whether the drill of the passage is implemented correctly or whether the pedicle screw is implanted correctly, as any deviation from the pre-planned trajectory may cause damages to the surrounding tissues.

It is noted that in the conventional methods, the surgeon needs to focus on both an affected part of the patient and the screen during the surgery.

SUMMARY

Therefore, an object of the disclosure is to provide a robotic surgical system that is configured to control a robot arm to automatically move according to a pre-planned surgical path, and to generate an augmented reality (AR) image of a three dimensional model of an affected part of a patient to be presented on a wearable device for a user.

According to the one embodiment of the disclosure, the robotic surgical system is adapted to be operated by a person to perform a surgical operation on a patient in a workspace. For providing reference for processing, a dynamic reference frame (DRF) is disposed on an affected part of the patient in a manner that a relative location of the affected part and the DRF remains unchanged. The robotic surgical system includes a surgical robot, a wearable device, a camera and a computer device.

The surgical robot includes a movable platform, a robot base mounted on the movable platform, and a robotic arm extending from the robot base. The movable platform has a base marker mounted thereon. The robotic arm has one end that is connected to the robot base, and another end that holds a surgical instrument.

The wearable device is to be worn by the person.

The camera is disposed in the workspace for capturing images, and is associated with a navigation coordinate system (NCS).

The computer device is coupled to the surgical robot, the wearable device and the camera, and stores therein data of a three-dimensional (3D) model associated with the affected part of the patient, and data of a pre-planned surgical path. The 3D model and the pre-planned surgical path are associated with a 3D coordinate system.

The camera is configured to capture images of the base marker and the DRF, and transmit the images to the computer device for processing.

The computer device is configured to:
use the images that contain the DRF and that are captured by the camera to obtain a conversion relationship between the NCS and a reference coordinate system associated with the DRF;
based on the conversion relationship between the NCS and the reference coordinate system and a conversion relationship between the 3D coordinate system and the reference coordinate system, calculate a conversion relationship between a set of coordinates of a target point of the pre-planned surgical path and a set of coordinates of a corresponding real-world point in a base coordinate system associated with the robot base;
based on the conversion relationship between the target point of the pre-planned surgical path and the corresponding real-world point, control the robotic arm to move the surgical instrument according to the pre-planned surgical path;
calculate a conversion relationship between the DRF and a device coordinate system associated with the wearable device, and calculate a conversion relationship between the 3D coordinate system and the device coordinate system, based on the conversion relationship between the DRF and the device coordinate system associated with the wearable device and the conversion relationship between the 3D coordinate system and the reference coordinate system associated with the DRF; and
transmit the data of the 3D model and the data of the pre-planned surgical path to the wearable device, such that the wearable device is configured to present the 3D model in combination with the pre-planned surgical path as an AR image based on the conversion relationship between the 3D coordinate system and the device coordinate system.

BRIEF DESCRIPTION OF THE DRAWINGS

Other features and advantages of the disclosure will become apparent in the following detailed description of the embodiment(s) with reference to the accompanying drawings. It is noted that various features may not be drawn to scale.

DETAILED DESCRIPTION

Figure 1:
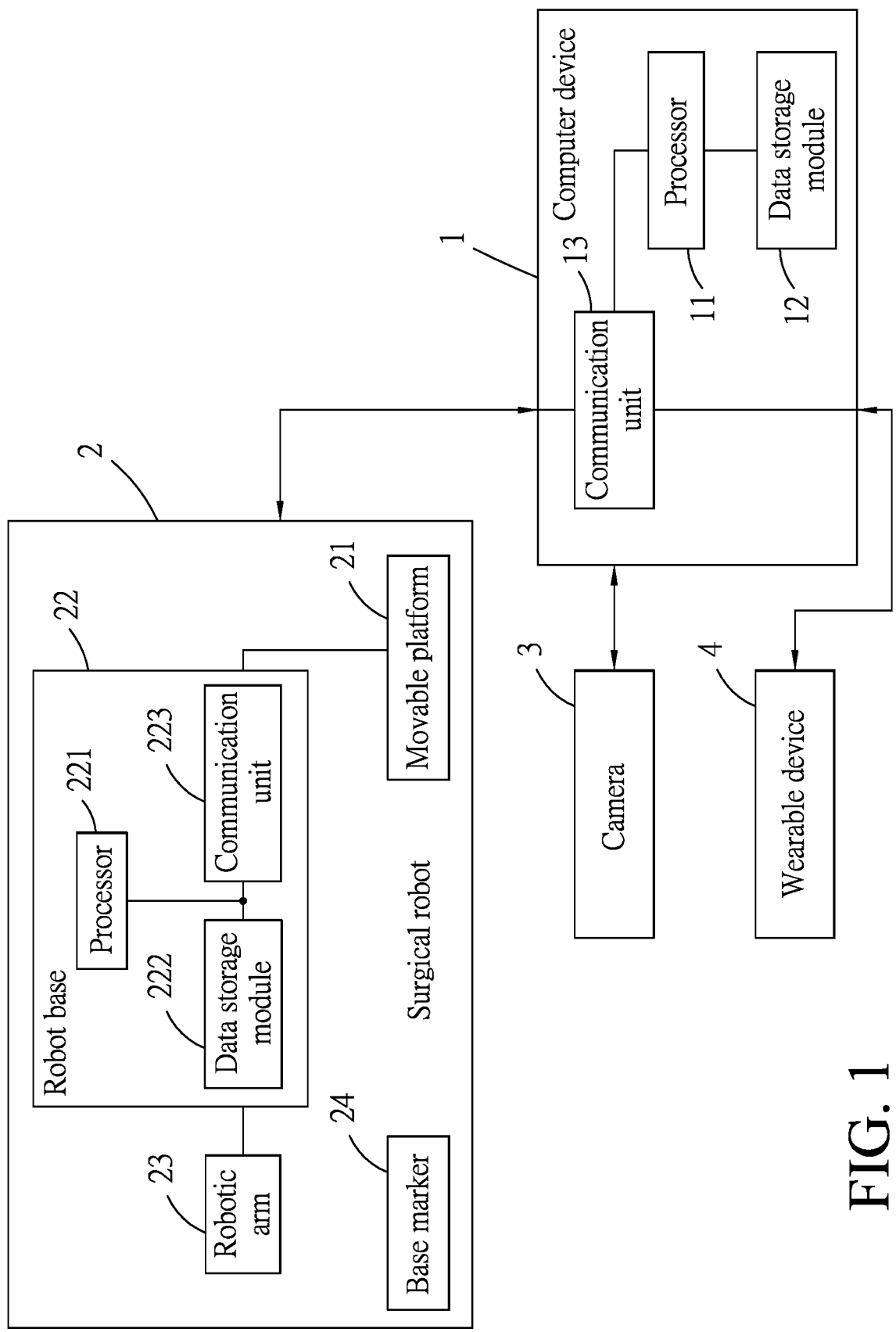
FIG. 1 is a block diagram illustrating a robotic surgical system according to one embodiment of the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Throughout the disclosure, the term "coupled to" or "connected to" may refer to a direct connection among a plurality of electrical apparatus/devices/equipment via an electrically conductive material (e.g., an electrical wire), or an indirect connection between two electrical apparatus/devices/equipment via another one or more apparatus/devices/equipment, or wireless communication.

FIG. 1 is a block diagram illustrating a robotic surgical system according to one embodiment of the disclosure. In this embodiment, the robotic surgical system includes a computer device 1, a surgical robot 2, a camera 3 and a wearable device 4.

The computer device 1 may be embodied using a personal computer, a laptop, a server, or other electronic devices that are equipped with computing functions. The computer device 1 includes a processor 11, a data storage module 12, and a communication unit 13.

The processor 11 is connected to the data storage module 12 and the communication unit 13.

The processor 11 may include, but not limited to, a single core processor, a multi-core processor, a dual-core mobile processor, a microprocessor, a microcontroller, a digital signal processor (DSP), a field-programmable gate array (FPGA), and/or an application specific integrated circuit (ASIC), etc.

The data storage module 12 may be embodied using, for example, random access memory (RAM), read only memory (ROM), programmable ROM (PROM), firmware, and/or flash memory, etc. In this embodiment, the data storage module 12 stores a software application that includes instructions that, when executed by the processor 11, cause the processor 11 to implement operations as described below.

Figure 4:
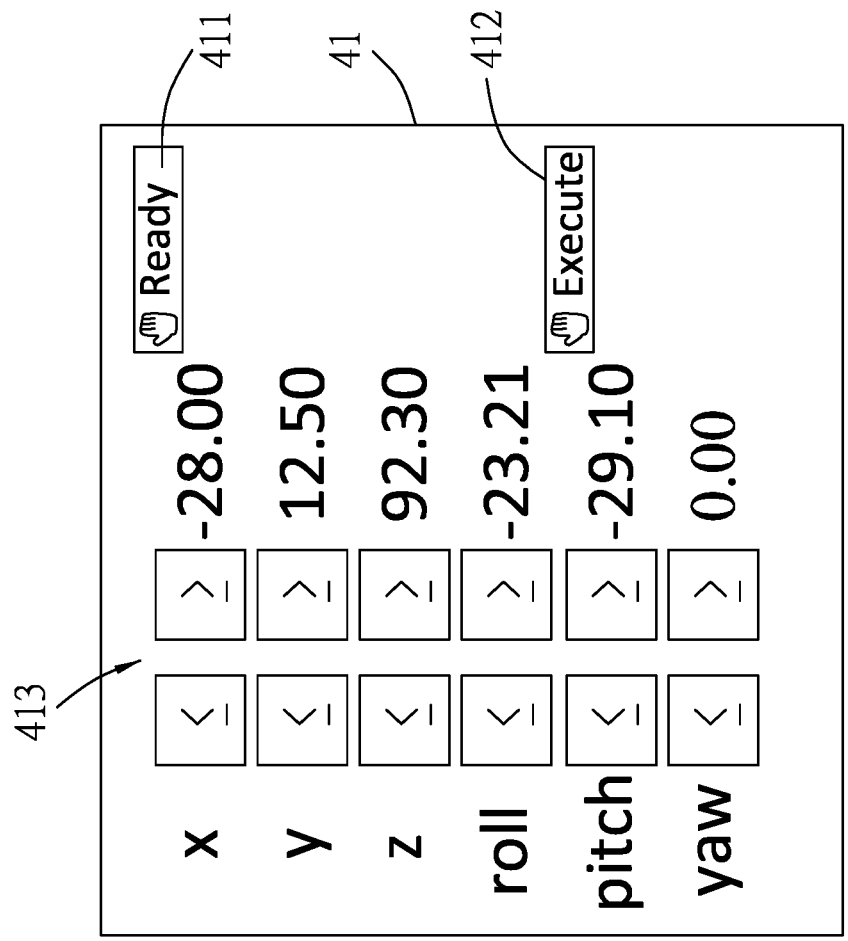
FIG. 4 illustrates an exemplary manner in which various content, including an AR image and a virtual interface, is presented by the wearable device to be seen by a person wearing the same according to one embodiment of the disclosure.
Figure 4:
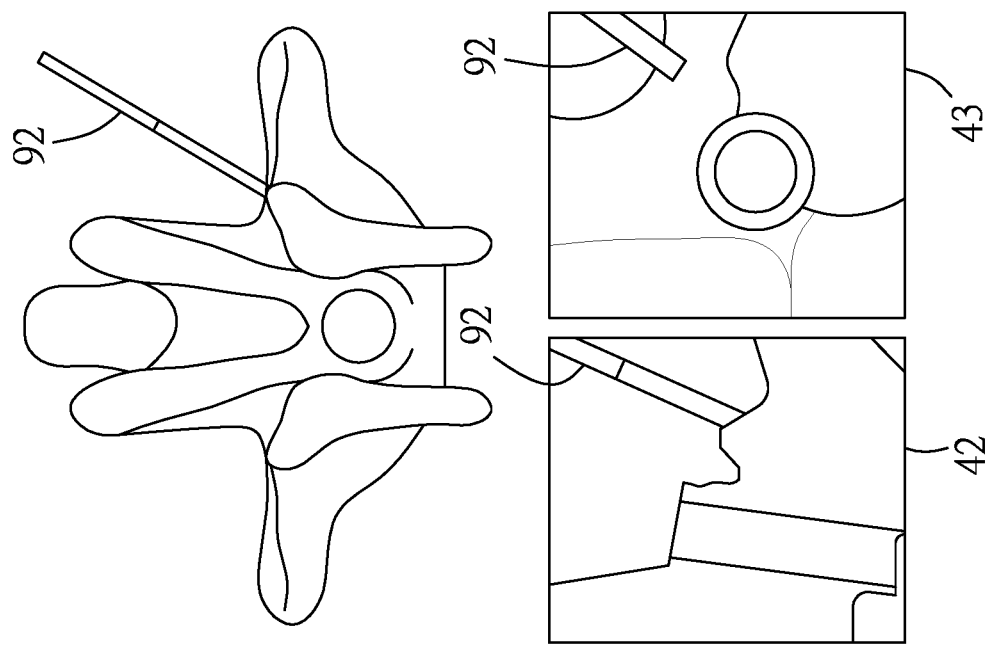

In addition, the data storage module 12 stores therein data of a three-dimensional (3D) model associated with an affected part 90 (see FIG. 2) of a patient, and data of a pre-planned surgical path 92 (see FIG. 4). The 3D model may be constructed using images of the affected part 90 obtained by computerized tomography (CT) scanning, and is associated with a 3D coordinate system O1. The pre-planned surgical path 92 may include a plurality of points represented using the 3D coordinate system O1. In this embodiment, the points may be connected to yield a line (e.g., a straight line) that goes inside the 3D model associated with the affected part 90, so as to enable a surgical drill to move accordingly. The pre-planned surgical path 92 is designed such that the surgical drill can move inside the affected part 90 without contacting the more critical parts of the patient (e.g., the spinal cord, nerve roots, etc.).

The communication unit 13 may include one or more of a radio-frequency integrated circuit (RFIC), a short-range wireless communication module supporting a short-range wireless communication network using a wireless technology of Bluetooth® and/or Wi-Fi, etc., and a mobile communication module supporting telecommunication using Long-Term Evolution (LTE), the third generation (3G), the fourth generation (4G) or fifth generation (5G) of wireless mobile telecommunications technology, or the like. In this embodiment, the computer device 1 is coupled to the surgical robot 2, the camera 3 and the wearable device 4 via the communication unit 13.

Figure 2:
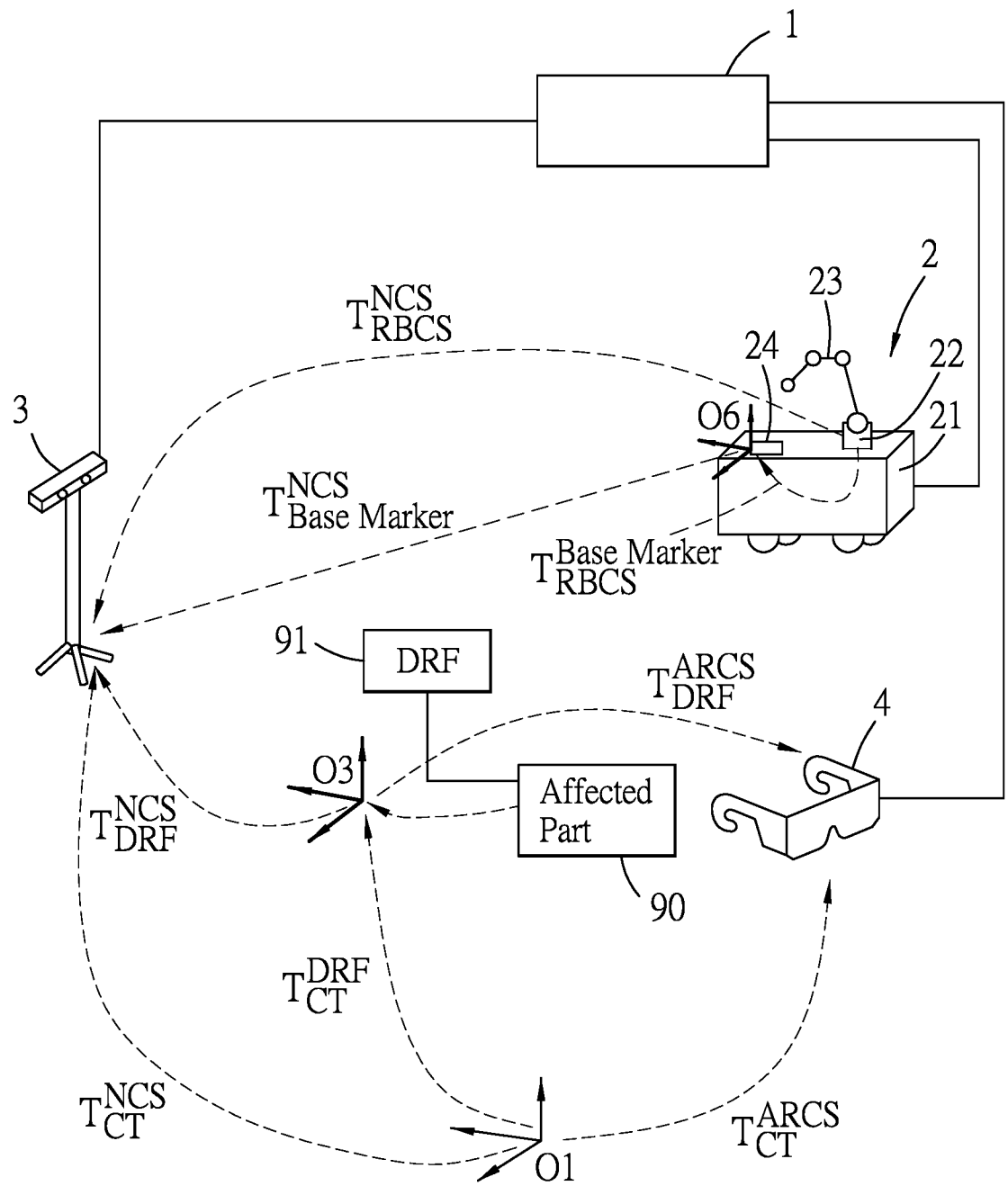
FIG. 2 illustrates the components of the robotic surgical system being placed in a workspace, and coordinate relationships among the components of the robotic surgical system and a three-dimensional (3D) model according to one embodiment of the disclosure.

FIG. 2 illustrates the components of the robotic surgical system being placed in a workspace (e.g., an operating room (OR)), and coordinate relations among the components of the robotic surgical system according to one embodiment of the disclosure. The OR may include an operating table for allowing a patient to lie thereon. The patient has an affected part 90 that needs a surgical operation. In embodiments, the affected part 90 may be a pediculus arcus vertebrae, and the surgical operation may be a pedicle screw placement. It is noted however that the robotic surgical system may be implemented for other surgical operations.

In use, a dynamic reference frame (DRF) 91 is disposed on the affected part 90 in a manner that a relative location of the affected part 90 and the DRF 91 remains unchanged. For example, in some embodiments, the DRF 91 is secured on the affected part 90 using a clamp or a locating pin. In some embodiments, the DRF 91 may include a two-dimensional code, such as an AprilTag, a quick response (QR) code, etc.

The surgical robot 2 includes a movable platform 21, a robot base 22 mounted on the movable platform 21, and a robotic arm 23 extending from the robot base 22. Referring to FIGS. 1 and 2 simultaneously, the robot base 22 may include a processor 221 that enables control of movement of the robotic arm 23, a data storage module 222, and a communication unit 223 that enables communication with the computer device 1. The processor 221, the data storage module 222 and the communication unit 223 may be embodied using components that are similar to the processor 11, the data storage module 12 and the communication unit 13, respectively.

The robotic arm 23 may be embodied using a six-axis robotic arm that is configured to move with six degrees of freedom. The robotic arm 23 has one end that is connected to the robot base 22, and another end that is configured to hold a surgical instrument (e.g., a surgical drill).

A base marker 24 is mounted on the movable platform 21. In some embodiments, the base marker 24 may include a two-dimensional code, such as an AprilTag, a QR code, etc.

The camera 3 is disposed in the workspace for capturing images, and includes a communication unit (not shown) for communicating with the computer device 1. In this embodiment, the camera 3 may be embodied using a RealSense D435 depth camera manufactured by Intel Corporation, but may be embodied using various other cameras in other embodiments. In use, the movable platform 21, the patient and the camera 3 are positioned in a manner that the camera 3 is configured to capture images of the base marker 24 and the DRF 91, and transmit the images to the computer device 1 for processing (e.g., determination of locations and orientations of the base marker 24 and the DRF 91).

The wearable device 4 is configured to be worn by a person (e.g., a surgeon) and may be embodied using a set of glasses that supports augmented reality (AR) functionality. In this embodiment, the wearable device 4 is a Microsoft "HoloLens 2."

In use, the wearable device 4 may also include components such as a set of cameras for capturing images, a processor for rendering images such as AR images for viewing by the person, and a display for displaying the images.

Prior to the surgical operation, a preoperative registration process may be performed. Specifically, the preoperative registration process is done to align the 3D model with the affected part 90, such that the 3D model and the affected part 90 may be represented on a same coordinate system. In this embodiment, a relevant coordinate system is a navigation coordinate system (NCS) associated with the camera 3. To achieve this, a number of conversion relationships, which may be indicated by transformation matrices, among different coordinate systems will be obtained or calculated, and then utilized in the operations described in the following paragraphs. Using the conversion relationships, a set of coordinates of a specific point in one coordinate system can be converted to another set of coordinates in another coordinate system.

A number of feature points on the 3D model may be pre-selected by a user, and in the preoperative registration process, the user operates a probe to use a distal end of the probe to contact a number of feature points on the affected part 90 that correspond with the feature points on the 3D model, respectively. A visual marker (such as an AprilTag, a QR code, etc.) is disposed on the probe, and the camera 3 is activated so as to capture images of the probe being in contact with each of the feature points on the affected part 90.

Since the relative location of the visual marker with respect to the distal end of the probe is unchanged during the preoperative registration process, the processor 11 of the computer device 1 is configured to, when receiving the images of the probe being in contact with each of the feature points on the affected part 90, determine the corresponding locations of the distal end of the probe (i.e., the feature points on the affected part 90) based on the corresponding locations of the visual marker in the NCS.

The processor 11 is configured to then perform a feature point matching operation to match the feature points on the affected part 90 in the NCS respectively to the corresponding feature points on the 3D model in the 3D coordinate system O1, so as to obtain an initial relation between the NCS and the 3D coordinate system O1.

In some embodiments, in addition to the feature point matching, the preoperative registration process may further include operating the probe to further move along a surface of the affected part 90, capturing images of the probe moving along the surface of the affected part 90 by using the camera 3, and analyzing locations of the visual marker on the probe in these images, so as to obtain a set of data points (also known as a point cloud) associated with the affected part 90 in the NCS. Using the point cloud associated with the affected part 90 and the initial relation between the NCS and the 3D coordinate system O1, an iterative closest point (ICP) matching operation may be implemented to obtain a conversion relationship between the NCS and the 3D coordinate system O1, which is relatively more accurate than the initial relation between the NCS and the 3D coordinate system O1. It is noted that a number of pre-processing operations may be performed with respect to the point cloud before performing the ICP matching operation, such as outlier removal, down-sampling (using, for example, Voxel grid filter), moving lease square smoothing, surface normal estimation, etc.

As shown in FIG. 2, the DRF 91 is associated with a reference coordinate system O3. Since the relative location of the affected part 90 with respect to the DRF 91 is unchanged, a conversion relationship between the affected part 90 and the 3D model may be obtained by obtaining a conversion relationship between the 3D coordinate system O1 and the reference coordinate system O3. The conversion relationship between the 3D coordinate system O1 and the reference coordinate system O3 may be obtained based on a conversion relationship between the reference coordinate system O3 and the NCS and the conversion relationship between the NCS and the 3D coordinate system O1 obtained previously. It is noted that the conversion relationship between the reference coordinate system O3 and the NCS may be obtained using images that contain the DRF 91 captured by the camera 3 (e.g., by detecting locations of the DRF 91 in the images captured by the camera 3).

Specifically, the conversion relationship TN F between the 3D coordinate system O1 and the reference coordinate system O3 may be represented using the following equation:

$$T_{CT}^{DRF} = T_{DRF}^{NCS^{-1}} T_{CT}^{NCS},$$

where $T_{DRF}^{NCS^{-1}}$ represents an inverse transformation matrix indicating the conversion relationship between the reference coordinate system O3 and the NCS (which may be represented using $T_{DRF}^{NCS}$), and $T_{CT}^{NCS}$ represents the conversion relationship between the NCS and the 3D coordinate system O1.

As such, the 3D model is considered to be "registered" with the DRF 91, and using the conversion relationship between the DRF 91 and the 3D model (i.e., the conversion relationship TN F between the 3D coordinate system O1 and the reference coordinate system O3), the processor 11 may be capable of "tracking" the affected part 90 during the surgical operation by virtue of the DRF 91 that is secured on the affected part 90. That is to say, even when the affected part 90 is moved during the surgical operation, the processor 11 may be capable of calculating a coordination between each set of coordinates of the 3D model and a corresponding set of coordinates of the affected part 90, that is, the 3D model may be moved along with the affected part 90 so as to be aligned with the affected part 90.

It is noted that when the DRF 91 is unintentionally moved with respect to the affected part 90 during the surgical operation, the above operations are to be implemented again.

In another embodiment, the DRF 91 is embodied using an optical tracker (e.g., the Polaris Vega manufactured by Northern Digital Inc.) or a cylindrical component formed with specific grooves (e.g., one manufactured by EPED Inc.). In the preoperative registration process, a user may instead operate a CT device to obtain an intraoperative 3D CT model of the affected part 90 and the DRF 91.

Figure 3:
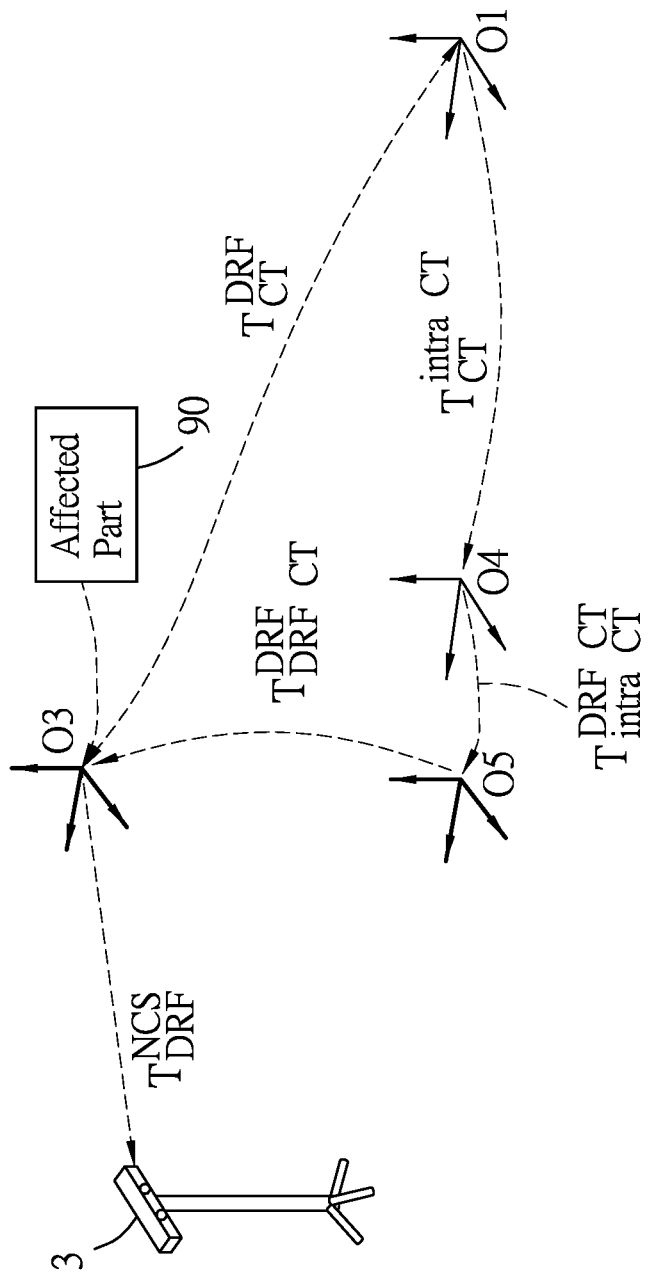
FIG. 3 illustrates coordinate relationships among the components of the robotic surgical system, the 3D model and an intraoperative 3D computerized tomography (CT) model according to one embodiment of the disclosure.

As shown in FIG. 3, the affected part 90 in the intraoperative 3D CT model is associated with an affected part (AP) coordinate system O4, and the DRF 91 in the intraoperative 3D CT model is associated with an intraoperative coordinate system O5. The processor 11 is configured to obtain a conversion relationship between the AP coordinate system O4 and the intraoperative coordinate system O5, represented using the transformation matrix $T_{intra\_CT}^{DRF\_CT}$ based on locations of the affected part 90 and the DRF 91 in the intraoperative 3D CT model.

Then, using a number of feature points on the DRF 91 and a number of corresponding feature points on the DRF 91 in the intraoperative 3D CT model, the processor 11 is configured to perform a feature point matching operation to match the feature points on the DRF 91 respectively to the corresponding feature points on the DRF 91 in the intraoperative 3D CT model, and to implement the ICP matching operation with the aid of a result of this feature point matching operation, so as to obtain a conversion relationship between the reference coordinate system O3 and the intraoperative coordinate system O5, represented using the transformation matrix $T_{DRF\_CT}^{DRF}$.

Afterward, the processor 11 is configured to perform a feature point matching operation to match the feature points on the affected part 90 of the 3D model respectively to the corresponding feature points on the affected part 90 in the intraoperative 3D CT model, and to implement the ICP matching operation with the aid of a result of this feature point matching operation, so as to obtain a conversion relationship between the 3D model and the intraoperative 3D CT model, represented using the transformation matrix $T_{CT}^{intra\_CT}$.

Using the above relationships, a conversion relationship between the DRF 91 and the 3D model (the 3D coordinate system O1) may be represented using the following equation:

$$T_{CT}^{DRF} = T_{DRF\_CT}^{DRF} T_{intra\_CT}^{DRF\_CT} T_{CT}^{intra\_CT}.$$

Using the images of the DRF 91 captured by the camera 3, the processor 11 is configured to obtain a conversion relationship between the reference coordinate system O3 and the NCS, represented using the transformation matrix $T_{DRF}^{NCS}$. Then, using the conversion relationship of the reference coordinate system O3 and the NCS and the conversion relationship between the DRF 91 and the 3D model, the processor 11 is configured to obtain a conversion relationship between the NCS to the 3D model, represented using the following equation:

$$T_{CT}^{NCS} = T_{DRF}^{NCS} T_{CT}^{DRF}.$$

Using the above equation, the processor 11 is configured to convert a set of coordinates representing a specific point on the 3D model into to a set of coordinates in the NCS associated with the camera 3.

Then, the processor 11 is configured to control the surgical robot 2 to move the surgical instrument along the pre-planned surgical path 92, so as to perform the surgical operation. Since the pre-planned surgical path 92 is designed with respect to the 3D model, additional conversion operations among the coordinate systems is needed. As shown in FIG. 2, the movable platform 21 of surgical robot 2 is associated with a platform coordinate system O6.

In this embodiment, the processor 11 is configured to implement a conversion operation using the following equation:

$$T_{Target}^{RBCS} = T_{RBCS}^{BaseMarker^{-1}} T_{BaseMarker}^{NCS^{-1}} T_{DRF}^{NCS} T_{CT}^{DRF} T_{Target}^{CT}$$

where Target represents a set of coordinates of a target point that is associated with a corresponding point of the pre-planned surgical path 92 (to which the surgical robot 2 is moving the surgical instrument) and that is associated with the 3D coordinate system O1, RBCS represents a base coordinate system associated with the robot base 22, the transformation matrix $T_{Target}^{RBCS}$ represents a conversion relationship between the set of coordinates of a target point and a set of coordinates of a corresponding real-world point in the RBCS, Base-Marker represents the platform coordinate system O6 associated with the base marker 24 mounted on the movable platform 21, the transformation matrix $T_{RBCS}^{BaseMarker}$ represents a conversion relationship between the platform coordinate system O6 and the RBCS, and the transformation matrix $T_{Target}^{CT}$ represents a conversion relationship between the pre-planned surgical path 92 and the 3D model within the 3D coordinate system O1. This conversion relationship between the pre-planned surgical path 92 and the 3D model within the 3D coordinate system O1 may be pre-established by the person after the 3D model and the pre-planned surgical path 92 are created.

As such, based on the above conversion relationships, the processor 11 is capable of performing a converting operation to convert the set of coordinates of the target point included in the pre-planned surgical path 92 to the set of coordinates of the corresponding real-world target point with respect to the RBCS, and control the robotic arm 23 to move the surgical instrument accordingly.

In the meantime, the set of cameras disposed on the wearable device 4, which is worn by the person, is configured to capture images of the workspace during the surgical operation with the DRF 91 being contained in the images. The images are then processed to detect the DRF 91, and the processor of the wearable device 4 is configured to calculate a conversion relationship between the DRF 91 and the wearable device 4, represented by the transformation matrix $T_{DRF}^{ARCS}$, where ARCS represents a device coordinate system associated with the wearable device 4.

Using the above conversion relationships, during the surgical operation, the processor of the wearable device 4 is configured to calculate a conversion relationship between the 3D model, in combination with the pre-planned surgical path 92, in the 3D coordinate system O1 and the ARCS. Such a conversion relationship $T_{CT}^{ARCS}$ may be represented using the following equation:

$$T_{CT}^{ARCS} = T_{DRF}^{ARCS} T_{CT}^{DRF}.$$

As such, the processor of the wearable device 4 is configured to present, via the display, the 3D model in combination with the pre-planned surgical path 92 as an AR image to be "superimposed" over the affected part 90 in the point-of-view of the person based on the above conversion relationship $T_{CT}^{ARCS}$. In this manner, the person may be enabled to supervise the surgical operation performed by the surgical robot 2, and to determine whether the surgical robot 2 is moving the surgical instrument along the pre-planned surgical path 92.

In embodiments, the wearable device 4 is configured to present a virtual interface for the person. FIG. 4 illustrates an exemplary manner in which different content, including the AR image and the virtual interface, is presented by the wearable device 4 to be seen by the person wearing the wearable device 4 according to one embodiment of the disclosure.

In the embodiment of FIG. 4, the virtual interface includes a control screen 41 and two sub-screens 42, 43. The control screen 41 includes a plurality of virtual buttons. Specifically, the plurality of virtual buttons include a ready button 411, an execute button 412, and a number of sets of adjustment buttons 413 (six sets are present in the example of FIG. 4 to correspond with the six-degree-freedom configuration of the robotic arm 23). The control screen 41 is designed to enable the person to adjust the pre-planned surgical path 92, so as to address any potential situation that calls for adjustment of the pre-planned surgical path 92 (e.g., the patient and/or the movable platform 21 being moved).

Specifically, when the ready button 411 is pressed, the processor of the wearable device 4 generates an initialize signal and transmits the initialize signal to the computer device 1. In turn, the processor 11 of the computer device 1 sets the pre-planned surgical path 92 to an initial state (i.e., unchanged). The sets of adjustment buttons 413 enable the person to adjust the pre-planned surgical path 92 in different manners. For example, three sets of adjustment buttons 413 with labels "X", "Y" and "Z" enable shifts of the planned surgical path 92 along an x-axis, a y-axis and a z-axis, respectively. Three sets of adjustment buttons 413 with labels "roll", "pitch" and "yaw" enable rotations of the pre-planned surgical path 92 about a roll-axis, a pitch-axis and a yaw-axis, respectively. In use, in response to the person operating the sets of adjustment buttons 413, an adjusted surgical path may be calculated and presented on the AR image and/or the sub-screens 42, 43.

After manual adjustment of the pre-planned surgical path 92 is complete, the person may press the execute button 412 in order to initiate the surgical operation. In turn, the processor of the wearable device 4 may transmit data of the adjusted surgical path to the computer device 1. In response, the processor 11 of the computer device 1 may store the data of the adjusted surgical path in the data storage module 12 as the data of the pre-planned surgical path 92. In this manner, the person wearing the wearable device 4 is enabled to adjust the pre-planned surgical path 92, and subsequently the processor 11 of the computer device 1 is configured to control the surgical robot 2 to move the surgical instrument along the adjusted pre-planned surgical path 92.

It is noted that since the adjustment is made with respect to the 3D coordinate system O1, in use, the processor 11 of the computer device 1 is also configured to convert the coordinates of the points of the adjusted pre-planned surgical path 92 to the RBCS, based on the conversion relationships calculated in the above operations.

The sub-screens 42, 43 display a partial sectional view of a preset location of the 3D model and a top view of the preset location of the 3D model, respectively. In addition, the pre-planned surgical path 92 is also visible in the sub-screens 42, 43. It is noted that in other embodiments, the wearable device 4 may display only one sub-screen, or may display additional sub-screens that include other views of the 3D model. In use, the views displayed on the sub-screens 42, 43 may assist the person in determining whether the pre-planned surgical path 92 is appropriate. In the cases where the person determines that the pre-planned surgical path 92 needs to be adjusted, he/she may operate the control screen 41 to adjust the pre-planned surgical path 92. It is noted that such operations may be done during the surgical operation.

Figure 5:
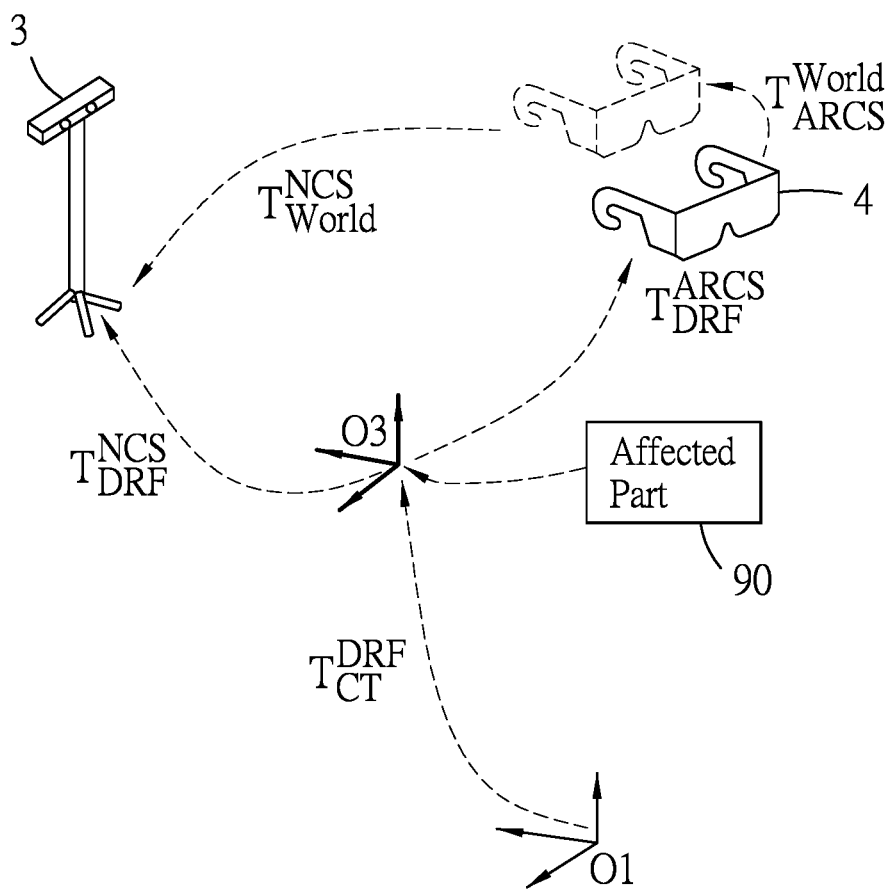
FIG. 5 illustrates coordinate relationships among the components of the robotic surgical system, the 3D model and a world coordinate system according to one embodiment of the disclosure.

In some embodiments, the wearable device 4 may be equipped with a spatial awareness functionality. Specifically, in the embodiment of FIG. 5, the wearable device 4 is embodied using the "Hololens 2," which is equipped with a plurality of visible light cameras (e.g., four) and a depth camera. As such, using the equipment of the wearable device 4, the processor of the wearable device 4 is configured to determine a conversion relationship between a world coordinate system associated with the workspace and the device coordinate system associated with the wearable device 4 (ARCS), represented by the transformation matrix $T_{ARCS}^{World}$, where World represents the world coordinate system.

In the cases that the DRF 91 is detected in the images captured by the wearable device 4, a conversion relationship between the world coordinate system and the NCS that is represented by the transformation matrix $T_{NCS}^{World} = T_{ARCS}^{World} T_{DRF}^{ARCS} T_{DRF}^{NCS^{-1}}$ may be determined by the computer device 1. Then, a conversion relationship $T_{CT}^{ARCS}$ between the 3D coordinate system O1 and the device coordinate system associated with the wearable device 4 may be calculated based on the conversion relationship between the world coordinate system associated with the workspace and the device coordinate system associated with the wearable device 4 (represented by $T_{ARCS}^{World}$) and the conversion relationship between the world coordinate system and the NCS (represented by $T_{NCS}^{World}$). The conversion relationship $T_{CT}^{ARCS}$ is represented using the following equation:

$$T_{CT}^{ARCS} = T_{ARCS}^{World^{-1}} T_{NCS}^{World} T_{DRF}^{NCS} T_{CF}^{DRF}.$$

In this manner, in the cases where the DRF 91 becomes temporarily blocked and cannot be detected in the images captured by the wearable device 4, the above conversion relationship may be implemented by the wearable device 4 to determine a location and/or orientation of the AR image presented to the person. Specifically, the images captured by the camera 3 may be used to "track" the DRF 91, and the specific location of the AR image to be presented can be calculated and presented in response even when the DRF 91 is temporarily blocked from the field of view of the wearable device 4. As such, the robotic surgical system may be configured to adjust locations of the AR image of the 3D model in real time.

To sum up, the embodiments of the disclosure provide a robotic surgical system that is configured to implement a number of functions. For example, using a number of conversion relationships among different coordinate systems, a 3D model of an affected part 90 of the patient, along with a pre-planned surgical path 92, can be registered (i.e., aligned) with the patient, such that the robotic arm 23 of the surgical robot 2 may be controlled to move a surgical instrument attached thereon along the pre-planned surgical path 92. That is to say, the robotic surgical system has the capability of automatically guiding the robotic arm 23 to move according to the pre-planned surgical path 92.

Also, with reference to the DRF 91 that is secured on a patient, the 3D model and the pre-planned surgical path 92 can be presented to a person wearing the wearable device 4 in the form of an AR image. As such, during the surgical operation, the person is enabled to determine whether the pre-planned surgical path 92 needs to be adjusted. Using this configuration, the person is not required to A virtual interface is also provided such that when it is determined that the pre-planned surgical path 92 needs to be adjusted, the person may operate the virtual interface to shift and/or rotate the pre-planned surgical path 92, so as to generate an adjusted surgical path. As such, the robotic arm 23 may be controlled to move the surgical instrument along the adjusted surgical path. Also, using this configuration, the person is not required to look away from the patient to adjust the pre-planned surgical path 92 during the surgical operation.

Additionally, in the cases where the DRF 91 becomes obscured or is otherwise missing from the images captured by the wearable device 4, using the spatial awareness functionality of the wearable device 4, the images captured by the camera 3 may be further utilized to determine the location of the DRF 91, and the location of the AR image may be adjusted and presented to the person in real time during the surgical operation.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects; such does not mean that every one of these features needs to be practiced with the presence of all the other features. In other words, in any described embodiment, when implementation of one or more features or specific details does not affect implementation of another one or more features or specific details, said one or more features may be singled out and practiced alone without said another one or more features or specific details. It should be further noted that one or more features or specific details from one embodiment may be practiced together with one or more features or specific details from another embodiment, where appropriate, in the practice of the disclosure.

While the disclosure has been described in connection with what is are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A robotic surgical system adapted to be operated by a person to perform a surgical operation on a patient in a workspace, a dynamic reference frame (DRF) being disposed on an affected part of the patient in a manner that a relative location of the affected part and the DRF remains unchanged, the robotic surgical system comprising:

a surgical robot that includes a movable platform, a robot base mounted on said movable platform, and a robotic arm extending from said robot base, said movable platform having a base marker mounted thereon, said robotic arm having one end that is connected to said robot base, and another end that holds a surgical instrument;

a wearable device worn by the person;

a camera disposed in the workspace for capturing images, said camera being associated with a navigation coordinate system (NCS); and a computer device that is coupled to said surgical robot, said wearable device and said camera, and that stores therein data of a three-dimensional (3D) model associated with the affected part of the patient, and data of a pre-planned surgical path, the 3D model and the pre-planned surgical path being associated with a 3D coordinate system;

wherein:

said camera is configured to capture images of the base marker and the DRF, and transmit the images to said computer device for processing;

said computer device is configured to:

use the images that contain the DRF and that are captured by the camera to obtain a conversion relationship between the NCS and a reference coordinate system associated with the DRF, based on the conversion relationship between the NCS and the reference coordinate system and a conversion relationship between the 3D coordinate system and the reference coordinate system, calculate a conversion relationship between a set of coordinates of a target point of the pre-planned surgical path and a set of coordinates of a corresponding real-world point in a base coordinate system associated with said robot base, based on the conversion relationship between the set of coordinates of the target point of the pre-planned surgical path and the set of coordinates of the corresponding real-world point, control said robotic arm to move the surgical instrument according to the pre-planned surgical path, calculate a conversion relationship between the DRF and a device coordinate system associated with said wearable device, and calculate a conversion relationship between the 3D coordinate system and the device coordinate system, based on the conversion relationship between the DRF and the device coordinate system associated with said wearable device and the conversion relationship between the 3D coordinate system and the reference coordinate system associated with the DRF, and transmit the data of the 3D model and the data of the pre-planned surgical path to said wearable device, such that said wearable device is configured to present the 3D model in combination with the pre-planned surgical path as an AR image based on the conversion relationship between the 3D coordinate system and the device coordinate system;

wherein the conversion relationship between the set of coordinates of the target point of the pre-planned surgical path and the set of coordinates of the corresponding real-world point, represented as $T_{Target}^{RBCS}$, is calculated using the equation:

$$T_{Target}^{RBCS} = T_{RBCS}^{BaseMarker^{-1}} T_{BaseMarker}^{NCS^{-1}} T_{DRF}^{NCS} T_{CT}^{DRF} T_{Target}^{CT}$$

where Target represents a set of coordinates of the target point that is associated with a corresponding point of the pre-planned surgical path and that is associated with the 3D coordinate system, RBCS represents the base coordinate system, BaseMarker represents a platform coordinate system associated with the base marker, the transformation matrix $T_{RBCS}^{BaseMarker}$ represents a conversion relationship between the platform coordinate system and the RBCS, $T_{DRF}^{NCS}$ represents the conversion relationship between the reference coordinate system and the NCS, $T_{CT}^{DRF}$ represents the conversion relationship between the 3D coordinate system and the reference coordinate system, and a transformation matrix $T_{Target}^{CT}$ represents a conversion relationship between the pre-planned surgical path and the 3D model within the 3D coordinate system;

wherein the conversion relationship $T_{CT}^{DRF}$ between the 3D coordinate system and the reference coordinate system is calculated using the equation:

$$T_{CT}^{DRF} = T_{DRF\_CT}^{DRF} T_{intra\_CT}^{DRF\_CT} T_{CT}^{intra\_CT}$$

where $T_{DRF\_CT}^{DRF}$ represents a conversion relationship between the reference coordinate system and an intraoperative coordinate system associated with an intraoperative 3D computerized tomography (CT) model of the affected part and the DRF, $T_{intra\_CT}^{DRF\_CT}$ represents a conversion relationship between an affected part (AP) coordinate system associated with the affected part of the intraoperative 3D CT model and the intraoperative coordinate system, and $T_{CT}^{intra\_CT}$ represents a conversion relationship between the 3D model and the intraoperative 3D CT model.

2. The robotic surgical system of claim 1, wherein:
said wearable device is configured to present a virtual interface for the person to manually adjust the pre-planned surgical path to result in an adjusted surgical path, the virtual interface including a control screen that includes plural sets of adjustment buttons, each of the plural sets of adjustment buttons enabling one of a shift and a rotation of the pre-planned surgical path along a specific axis of the 3D coordinate system; and
said wearable device is further configured to transmit data of the adjusted surgical path to said computer device, and said computer device is configured to store the data of the adjusted surgical path as the data of the pre-planned surgical path.

3. The robotic surgical system of claim 2, wherein:
the control screen includes six sets of adjustment buttons;
three sets of adjustment buttons enable shifts of the planned surgical path along an x-axis, a y-axis and a z-axis, respectively; and
three sets of adjustment buttons enable rotations of the pre-planned surgical path along a roll-axis, a pitch-axis and a yaw-axis, respectively.

4. The robotic surgical system of claim 3, wherein the virtual interface further includes at least one sub-screen for displaying one of a partial sectional view of a preset location of the 3D model and a top view of the preset location of the 3D model.

5. The robotic surgical system of claim 1, wherein said wearable device is configured to:
determine a conversion relationship between a world coordinate system associated with the workspace and the device coordinate system associated with said wearable device, and a conversion relationship between the world coordinate system and the NCS;
calculate a conversion relationship between the 3D coordinate system and the device coordinate system based on the conversion relationship between the world coordinate system associated with the workspace and the device coordinate system associated with said wearable device, and the conversion relationship between the world coordinate system and the NCS; and
use the conversion relationship between the 3D coordinate system and the device coordinate system to determine a location of the AR image presented to the person when the DRF is not contained in the images captured by said wearable device.

6. The robotic surgical system of claim 5, wherein:
the conversion relationship between the world coordinate system and the NCS, represented as $T_{NCS}^{World}$, is represented by the transformation matrix $$T_{NCS}^{World} = T_{ARCS}^{World} T_{DRF}^{ARCS} T_{DRF}^{NCS^{-1}}$$

where $T_{ARCS}^{World}$ represents the conversion relationship between the world coordinate system and the device coordinate system, and $T_{DRF}^{ARCS}$ represents the conversion relationship between the DRF and the device coordinate system associated with said wearable device; and
the adjustment of the AR image is implemented using a conversion relationship between the 3D coordinate system and the device coordinate system $T_{CT}^{ARCS}$, represented using $T_{CT}^{ARCS} = T_{ARCS}^{World^{-1}} T_{NCS}^{World} T_{DRF}^{NCS} T_{CT}^{DRF}$.

* * * * *